United States Patent

Ksoll et al.

Patent Number: 5,154,763
Date of Patent: Oct. 13, 1992

[54] STABILIZED AQUEOUS ALKYLDIKETENE EMULSIONS

[75] Inventors: Peter Ksoll, Dossenheim; Erwin Hahn, Heidelberg; Peter Wittmer, Neustadt; Andreas Hohmann, Ludwigshafen; Arnold De Clercq, Dirmstein; Ulrich Riebeling, Schifferstadt, all of Fed. Rep. of Germany

[73] Assignee: BASF Aktiengesellschaft, Ludwigshafen, Fed. Rep. of Germany

[21] Appl. No.: 639,093

[22] Filed: Jan. 9, 1991

[30] Foreign Application Priority Data

Jan. 18, 1990 [DE] Fed. Rep. of Germany ....... 4001237

[51] Int. Cl.$^5$ ............................................. D21H 3/34
[52] U.S. Cl. ............................. 106/287.2; 106/213; 106/243; 162/158; 162/175
[58] Field of Search ................. 106/212, 213, 287.2, 106/243; 162/158, 175

[56] References Cited

U.S. PATENT DOCUMENTS

| T936,003 | 7/1976 | Watkins et al. |
|---|---|---|
| 2,627,477 | 2/1953 | Downey |
| 2,901,371 | 8/1959 | Arlt, Jr. |
| 3,130,118 | 4/1964 | Chapman |
| 3,311,532 | 3/1967 | Kulick et al. |
| 4,522,686 | 6/1985 | Dumas ........................ 106/218 |

FOREIGN PATENT DOCUMENTS

| 0093321 | 11/1983 | European Pat. Off. |
|---|---|---|
| 0327215 | 8/1989 | European Pat. Off. |
| 57-167492 | 10/1982 | Japan ........................ 106/287.2 |

Primary Examiner—Theodore Morris
Assistant Examiner—David M. Brunsman
Attorney, Agent, or Firm—Oblon, Spivak, McClelland, Maier & Neustadt

[57] ABSTRACT

Stabilized aqueous $C_{14}$–$C_{22}$-alkyldiketene emulsions containing, as essential components:
(a) from 10 to 60% w/w of at least one $C_{14}$–$C_{22}$-alkyldiketene,
(b) from 1 to 10% w/w of at least one protective colloid and
(c) from 0.1 to 20% w/w of at least one ester of formula I $$R^1-\underset{\underset{O}{\|}}{C}-O-R^2 \quad (I)$$

in which $R^1$ and $R^2$ each denote $C_{14}$–$C_{22}$-alkyl, $R^1$ differing in this case from $R^2$ by at least 4 carbon atoms in the alkyl chain, and/or the same or different $C_{14}$–$C_{22}$-alkenyl groups, or at least one ester of the formula $R^3-O-CO-O-R^4$ (II), in which $R^3$ and $R^4$ are alkyl or alkenyl radicals of from 2 to 22 carbon atoms or at least one urethane of formula III $$R^5-O-\underset{\underset{O}{\|}}{C}-N\underset{R^7}{\overset{R^6}{\diagup}} \quad (III)$$

in which $R^5$, $R^6$ and $R^7$ are the same or different alkyl or alkenyl radicals of from 2 to 22 carbon atoms and one of the substituents $R^5$, $R^6$ and $R^7$ contains at least 12 carbon atoms, and showing a ratio of emulsified components (a):(c) from 200:1 to 1:1 and the use of compounds of formulae I to III as stabilizers for the preparation of alkyldiketene emulsions containing at least 10% w/w and preferably from 16 to 40% w/w of emulsified alkyldiketene.

8 Claims, No Drawings

STABILIZED AQUEOUS ALKYLDIKETENE EMULSIONS

The invention relates to stabilized aqueous alkyldiketene emulsions containing at least 10% w/w of an emulsified $C_{14}$–$C_{22}$-alkyldiketene and to the use of long-chain fatty acid esters acting as stabilizer in the preparation of alkyldiketene emulsions.

U.S. Pat. No. 2,627,477 discloses that alkyldiketenes containing at least 6 carbon atoms in the molecule can be emulsified in water with the aid of emulsifiers or organic thickening agents. The resulting diketene emulsions are agents for stock sizing paper. U.S. Pat. No. 3,130,118 reveals that alkyl diketenes containing at least 6 carbon atoms can be emulsified in water in the presence of cationic starch. The resulting low-concentration alkyldiketene emulsions have an adequate shelf-life, whereas aqueous emulsions having a concentration of fatty alkyldiketenes of more than 12% solidify relatively quickly.

A variety of substances has been used to stabilize aqueous fatty alkyldiketene emulsions prepared using cationic starch. For example, U.S. Pat. No. 2,901,371 and U.S. Pat. No. 3,311,532 describe the use of higher fatty acids and their anhydrides, amides, aldehydes and acid chlorides. In such cases, the concentration of fatty alkyldiketenes in the aqueous emulsions is below 10% w/w/.

EP-A 0,327,215 discloses aqueous emulsions which contain a ketene dimer, a non-reactive hydrophobic compound and a stabilizer. The solids content of the emulsions is from 5 to about 70% w/w, and the weight ratio of ketene dimer to non-reactive hydrophobic compound is from approximately 1:4 to 1:166. The emulsions are used for sizing cellulose fibers. According to the Examples, the concentrations of alkyldiketene dimer in the aqueous emulsions is not more than 6% by weight.

It is an object of the present invention to provide aqueous alkyldiketene emulsions which have a higher concentration of fatty alkyldiketenes than the prior alkyldiketene emulsions and which are stable on storage.

According to the invention, this object is achieved with stabilized aqueous $C_{14}$–$C_{22}$-alkyldiketene emulsions when these contain, as essential components:

(a) from 10 to 60% w/w of at least one $C_{14}$–$C_{22}$-alkyldiketene,
(b) from 1 to 10% w/w of at least one protective colloid and
(c) from 0.1 to 20% of at least one ester of formula I

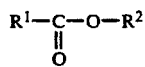

in which
(1) $R^1$ and $R^2$ each denote $C_{14}$–$C_{22}$-alkyl, $R^1$ differing from $R^2$ by at least 4 carbon atoms in the alkyl chain,
(2) $R^1$ is $C_{14}$–$C_{22}$-alkyl and $R^2$ is $C_{14}$–$C_{22}$-alkenyl,
(3) $R^1$ is $C_{14}$–$C_{22}$-alkenyl and $R^2$ is $C_{14}$–$C_{22}$-alkyl or
(4) $R^1$ and $R^2$ are the same or different $C_{14}$–$C_{22}$-alkenyl groups, or of at least one carbonate of formula II

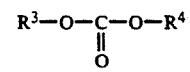

in which
$R^3$ and $R^4$ are the same or different alkyl or alkenyl radicals of from 2 to 22 carbon atoms and $R^3$ or $R^4$ has at least 6 carbon atoms, or of at least one urethane of formula III

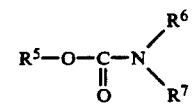

in which
$R^5$, $R^6$ and $R^7$ are the same or different alkyl or alkenyl radicals of from 2 to 22 carbon atoms and one of $R^5$, $R^6$ and $R^7$ contains at least 12 carbon atoms, and when the ratio of emulsified components (a):(c) is from 200:1 to 1:1.

The compounds of formulae I to III are, surprisingly, effective stabilizers for aqueous alkyldiketene emulsions having high solids contents, for example at least 10% and preferably at least 16%, by weight of alkyldiketene. They are therefore used as stabilizers for the preparation of aqueous $C_{14}$–$C_{22}$-alkyldiketene emulsions containing at least b 10% w/w/ of emulsified alkyldiketene. The amount of stabilizer used for this purpose is from 0.5 to 50% w/w, based on alkyldiketene.

Component (a) of the stabilized aqueous alkyldiketene emulsions comprises at least one $C_{14}$–$C_{22}$-alkyldiketene or a mixture of such alkyldiketenes. Said alkyldiketenes are known and are commercially available. They are prepared, for example, from the corresponding carboxylic chlorides by the removal of hydrogen chloride with tertiary amines. The fatty alkyldiketenes may be characterized, for example, by means of formula IV

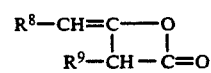

in which $R^8$ and $R^9$ are the same or different $C_{14}$–$C_{22}$-alkyl groups.

Suitable fatty alkyl diketenes are, for example, tetradecyldiketene, hexadecyldiketene, octadecyldiketene, eikosyldiketene, dokoyldiketene, palmityldiketene, stearyldiketene and behenyldiketene. Examples of compounds of formula IV in which the substituents $R^8$ and $R^9$ have different meanings are, for example, stearylpalmityldiketene, behenylstearyldiketene, behenyloleyldiketene and palmitylbehenyldiketene. Of the compounds of formula IV we prefer to use stearyl diketene, palmitryldiketene or mixtures of stearyl and palmitryl diketenes. The diketenes are present in the aqueous emulsions in concentrations of form 10 to 60%, preferably 16 to 404, by weight. Particularly preferred are those aqueous alkyldiketene emulsions which have concentrations ranging from 20 to 35% w/w of a $C_{14}$–$C_{22}$-alkyldiketene.

The alkyldiketenes are usually emulsified in water in the presence of a protective colloid. Suitable protective colloids have already been disclosed in the basic U.S. Pat. No. 2,626,477, for example sorbitan esters such as sorbitan monopalmitate, polyalkoxylated derivatives of sorbitan esters, anionic or non-ionic emulsifiers such as various soaps, synthetic detergents and thickening agents such as starches and water-soluble cellulose derivatives. Other suitable protective colloids for the preparation of said aqueous alkyldiketene emulsions are, for example, polymers of vinyl alcohol, acrylamide, vinylpyrrolidone or N-vinyl-2-methylimidzoline. We particularly prefer to use cationic starches as protective colloids. Suitable cationic starches for emulsifying fatty alkyldiketenes are described in U.S. Pat. No. 3,130,118 cited above and are commercially available. The amount of protective colloid, preferably cationic starch, is from 1 to 10% and preferably from 1.5 to 3%, by weight of the total emulsion.

According to the invention, the aqueous $C_{14}$–$C_{22}$-alkyldiketene emulsions containing protective colloid are stabilized by the use of at least one ester of formula (K)

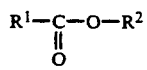

in which
- $R^1$ and $R^2$ each denote $C_{14}$–$C_{22}$-alkyl, $R^1$ differing from $R^2$ by at least 4 carbon atoms in the alkyl chain,
- $R^1$ is $C_{14}$–$C_{22}$-alkyl and
- $R^2$ is $C_{14}$–$C_{22}$-alkenyl,
- $R^1$ is $C_{14}$–$C_{22}$-alkenyl and
- $R^2$ is $C_{14}$–$C_{22}$-alkyl or $R^1$ and $R^2$ are the same or different $C_{14}$–$C_{22}$-alkenyl groups.

Compounds of formula I are known. Examples of suitable compounds of formula I in which $R^1$ and $R^2$ have the meanings stated under (1) above are behenyl stearate, stearyl behenate, stearlyl myristate, behenyl myristate, behenyl palmitate and isododecyl stearate.

Examples of compounds I in which $R^1$ and $R^2$ have the meanings stated under (2) are oleyl stearate, oleyl palmitate, oleyl behenate, oleyl myristate and oleyl arachate.

Examples of compounds I in which $R^1$ and $R^2$ have the meanings stated under (3) are stearyl oleate, behneyl oleate and palmityl oleate. Suitable compounds I in which $R^1$ and $R^2$ have the meanings stated under (4) are oleyl oleate, oleyl ricinolate, oleyl linolate and oleyl tallolate. Of the compounds of formula I we particularly prefer to use, as component (c) in the aqueous alkyldiketene emulsions, oleyl stearate and stearyl oleate.

The compounds of formula II ($R^3$—O—CO—$R^4$) are also known substances. $R^3$ and $R^4$ denote the same of different alkyl or alkenyl radicals, and at least one of the substituents $R^3$ and $R^4$ contains at least 6 carbon atoms. These substituents may contain 2 to 22 carbon atoms. If the substituents $R^3$ and $R^4$ are alkenyl, the alkenyl group preferably contains at least 6 carbon atoms. Examples of compounds of formula II are oleylstearyl carbonate, behenyloleyl carbonate, ethyloleyl carbonate, dioleyl carbonate, behenylstearyl carbonate and (2-hexyldecanyl)oleyl carbonate.

The compounds of the formula III

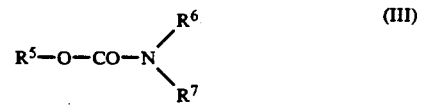

are also known substances, $R^6$, $R^6$ and $R^7$ denote the same or different substituents. They may contain from 2 to 22 carbon atoms and each stands for an alkyl or alkenyl group. At least one of $R^5$, $R^6$ and $R^7$ contains at least 12 carbon atoms. If these substituents are alkenyl groups, the number of carbon atoms in the alkenyl group is generally at least 12. Examples of compounds of formula III are oleyl-N,N-distearylurethane, palmitryl-N,N-distearylurethane, oleyl-N-palmitry-N-stearylurethane and behenyl-N,N-distearylurethane.

The compounds of group (c) are present in the aqueous alkyldiketene emulsions in concentrations ranging from 0.1 to about 20% and preferably from 1 to 10% by weight. Stabilization of, in particular, $C_{16}$–$C_{20}$-alkyldiketene emulsions having a concentration of from 20 to 35% w/w is generally effected using a compound of group (c) in an amount of from 2 to 8% w/w, based on the emulsion.

The compounds described under (a) and (c) above are present in the stabilized emulsion in a ratio of from 200:1 to 1:1, preferably from 20:1 to 2:1. The emulsions are prepared in conventional manner in conventional; apparatus by emulsifying the hydrophobic components in an aqueous solution of the protective colloid. Suitable apparatus includes, for example, homogenizers operating on the principle of decompression from high pressure, e.g. Lab 100 (APB Gaulin).

The general procedure is as follows: the solid diketene is melted and added to an aqueous solution of a protective colloid heated at 80°–85° C., the mixture being homogenized by the application of shearing forces. When preparing the alkyldiketene emulsions, the esters of formula I may be added to the aqueous solution of protective colloid and homogenized therewith either separately from or together with the molten alkyldiketene. The emulsion obtained after homogenization is cooled to ambient temperature. The pH of the alkyldiketene emulsions ranges from 2.9 to 3.1 and is preferably 3.0. When preparing said alkyldiketene emulsions it is possible, if desired, to add other auxiliaries such as lignin sulfonate, formalin or propionic acid.

Prior to use as stock sizing agents for paper, the concentrated alkyldiketene emulsions are diluted by the addition of water to give an alkyldiketene concentration of from 0.08 to 0.5% w/w/.

In the following Examples, the parts and percentages are by weight.

EXAMPLE 1

A 2% aqueous suspension of a commercial cationic starch (degree of substitution 0.02) is first prepared by suspending the required amount of cationic starch in water and then adding sufficient sulfuric acid to give a pH of 3. The starch suspension is then heated to 95° C. over a period of 1 hour and stirred at this temperature for a further hour, after which the resulting aqueous suspension is allowed to cool.

To 78 parts of the above 2% aqueous starch suspension heated 85° C. there is added a melt, heated at 90° C., of 20 parts of stearyldiketene and 2 parts of oleyl stearate, and the mixture is treated for 3 minutes in a Turrax. The emulsion is then homogenized twice at a temperature of 70° C. and under a pressure of 150 bar in a Lab 100 and then cooled to room temperature. There was obtained a stable, 20% aqueous stearyldiketene emulsion which remained stable after storage at 20°-25° C. for 30 days. No creaming or solidification of the emulsion could be observed.

EXAMPLE 2

Example 1 was repeated except that 20 parts of stearyldiketene and 4 parts of stearyl oleate was added to 76 parts of the starch suspension. There was obtained a stable, 20% aqueous stearyldiketene emulsion which remained stable after storage at 20°-25° C. for 30 days. No creaming or solidification of the emulsion was observed.

COMPARATIVE EXAMPLE

Example 1 was repeated except that the stearyldiketene was emulsified in the absence of oleyl stearate oleate. There was obtained an aqueous stearyl diketene emulsion which had a shelf life of only 4 days at 20°-25° C. At the end of this period the dispersion solidified.

EXAMPLE 3

Example 1 was repeated except that a melt of 20 parts of stearyldiketene and 8 parts of oleylstearyl carbonate were added to 72 parts of the starch suspension. There was obtained a stable, 30% aqueous stearyldiketene emulsion which remained stable after storage at 20°-25° C. for 30 days.

EXAMPLE 4

Example 1 was repeated except that in place of oleyl stearate the same amount of oleyl-N,N-distearylurethane was used. There was obtained a stable, 20% aqueous stearyldiketene emulsion which remained stable after storage at 20°-25° C. for 30 days.

EXAMPLE 5

Example 1 was repeated except that a melt of 30 parts of stearyldiketene and 4 parts of oleylstearyl carbonate was added to 66 parts of the starch suspension. There was obtained a stable, 20% aqueous stearyldiketene emulsion which remained stable after storage at 20°-25° C. for 30 days.

EXAMPLE 6

Example 1 was repeated except that a melt of 20 parts of stearyldiketene and 4 parts of oleyl oleate was added to 76 parts of the starch suspension. There was obtained a stable, 20% aqueous stearyldiketene emulsion which remained stable after storage at 20°-25° C. for 30 days.

EXAMPLE 7

Example 1 was repeated except that a melt of 30 parts of stearyldiketene and 6 parts of oleyl oleate was added to 64 parts of the starch suspension. There was obtained a stable, 30% aqueous stearyldiketene emulsion which remained stable after storage at 20°-25° C. for 30 days.

EXAMPLE 8

Example 1 was repeated except that a melt of 30 parts of stearyldiketene and 6 parts of dioleyl carbonate was added to 64 parts of the starch suspension. There was obtained a stable, 30% aqueous stearyldiketene emulsion which remained stable after storage at 20°-25° C. for 30 days.

EXAMPLE 9

Example 1 was repeated except that a melt of 20 parts of stearyldiketene and 10 parts of dioleyl carbonate was added to 70 parts of the starch suspension. There was obtained a stable, 20% aqueous stearyldiketene emulsion which remained stable after storage at 20°-25° C. for 30 days.

We claim:

1. A stabilized aqueous $C_{14}$–$C_{22}$-alkyldiketene emulsion containing, an essential components:
   (a) from 10 to 60% w/w of at least one $C_{14}$–$C_{22}$-alkyldiketene,
   (b) from 1 to 10% w/w of at least one protective colloid and
   (c) from 0.1 to 20% w/w of at least one ester of formula I $$R^1-C-O-R^2 \quad \text{(I)}$$
$$\underset{O}{\overset{\|}{}}$$

in which
   (1) $R^1$ and $R^2$ each denote $C_{14}$–$C_{22}$-alkyl, $R^1$ differing from $R^2$ by at least 4 carbon atoms in the alkyl chain,
   (2) $R^1$ is $C_{14}$–$C_{22}$-alkyl and $R^2$ is $C_{14}$–$C_{22}$-alkenyl,
   (3) $R^1$ is $C_{14}$–$C_{22}$-alkenyl and $R^2$ is $C_{14}$–$C_{22}$-alkyl
   or
   (4) $R^1$ and $R^2$ are the same or different $C_{14}$–$C_{22}$-alkenyl groups, or of at least one carbonate of formula II $$R^3-O-C-O-R^4 \quad \text{(II)}$$
$$\underset{O}{\overset{\|}{}}$$

in which
$R^3$ and $R^4$ are the same or different alkyl or alkenyl radicals of from 2 to 22 carbon atoms and $R^3$ or $R^4$ has at least 6 carbon atoms, or of at least one urethane of formula III $$R^5-O-C-N\begin{array}{c}R^6\\ \\R^7\end{array} \quad \text{(III)}$$
$$\underset{O}{\overset{\|}{}}$$

in which
$R^5$, $R^6$ and $R^7$ are the same or different alkyl or alkenyl radicals of from 2 to 22 carbon atoms and one of $R^5$, $R^6$ and $R^7$ contains at least 12 carbon atoms, and showing a ratio of emulsified components (a):(c) from 200:1 to 1:1.

2. A stabilized aqueous $C_{14}$–$C_{22}$-alkyldiketene emulsion as claimed in claim 1 and containing:
   (a) from 16 to 40% w/w of at least one $C_{14}$–$C_{22}$-alkyldiketene,
   (b) from 1 to 4% w/w of at least one cationic starch and
   (c) from 1 to 10% w/w of at least one ester, carbonate of formula I or II or urethane of formula III.

3. A stabilized aqueous $C_{14}$–$C_{22}$-alkyl diketene emulsion containing as essential components:
   (a) from 10%–60% w/w of at least one $C_{14}$–$C_{22}$-alkyl diketene,
   (b) from 1 to 10% w/w of at least one protective colloid, and
   (c) from 0.1 to 20% w/w of at least one compound selected from the group consisting of:
   behenyl stearate, stearyl behenate, oleyl stearate, stearyl oleate, behenyl oleate, oleyl oleate, oleylstearyl carbonate, behenyloleyl carbonate, behenylstearyl carbonate, dioleyl carbonate, oleyl-N,-distearylurethane and mixtures thereof,
   the ratio of emulsified components (a):(c) being form 200:1 to 1:1.

4. A stabilized aqueous $C_{14}$–$C_{22}$-alkyldiketene emulsion as claimed in claim 1, wherein the component (c) contained therein is at least one compound selected from the group consisting of
   behenyl stearate,
   stearyl behenate,
   oleyl stearate,
   stearyl oleate,
   benhenyl oleate,
   oleyl oleate,
   and mixtures thereof.

5. A stabilized aqueous $C_{14}$–$C_{22}$-alkyldiketene emulsion as claimed in claim 1, 2 or 3 wherein the component (c) contained therein is at least one compound selected from the group consisting of
   oleylstearyl carbonate,
   behenyloleyl carbonate,
   behenylstearyl carbonate,
   dioleyl carbonate,
   and mixtures thereof.

6. A stabilized aqueous $C_{14}$–$C_{22}$-alkyldiketene emulsion as claimed in claim 1, 2 or 3 wherein the component (c) contained therein is oleyl-N,N-distearylurethane.

7. A stabilized aqueous stearyldiketene emulsion as claimed in claim 1, 2 or 3 which contains
   (a) from 20 to 40% w/w of stearyldiketene,
   (b) from 1 to 4% w/w of at least one cationic starch, and
   (c) from 1 to 8% of oleyl oleate.

8. A stabilized aqueous $C_{14}$–$C_{22}$-alkyl diketene emulsion as claimed in claim 1, 2 or 3, consisting essentially of said components (a), (b) and (c).

* * * * *